(12) United States Patent
Gentz

(10) Patent No.: US 12,280,246 B2
(45) Date of Patent: Apr. 22, 2025

(54) POWER SUPPLY FOR DRUG DELIVERY SYSTEMS

(71) Applicant: Ypsomed AG, Burgdorf (CH)

(72) Inventor: Michael Gentz, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 1217 days.

(21) Appl. No.: 17/029,900

(22) Filed: Sep. 23, 2020

(65) Prior Publication Data

US 2021/0008294 A1 Jan. 14, 2021

Related U.S. Application Data

(63) Continuation of application No. PCT/IB2019/052471, filed on Mar. 27, 2019.

(30) Foreign Application Priority Data

Mar. 29, 2018 (EP) .................................. 18164883

(51) Int. Cl.
*A61M 5/20* (2006.01)
*A61M 5/315* (2006.01)

(52) U.S. Cl.
CPC ....... *A61M 5/31568* (2013.01); *A61M 5/2033* (2013.01); *A61M 2205/3584* (2013.01);
(Continued)

(58) Field of Classification Search
CPC ............ A61M 5/31568; A61M 5/2033; A61M 2205/3584; A61M 2205/52; A61M 2205/581; A61M 2205/582
(Continued)

(56) References Cited

U.S. PATENT DOCUMENTS 3,701,345 A 10/1972 Heilman et al.
4,914,566 A 4/1990 Steutermann
(Continued)

FOREIGN PATENT DOCUMENTS

CN 101120618 A 2/2008
EP 3545991 A1 10/2019
(Continued)

OTHER PUBLICATIONS

International Preliminary Report on Patentability received for International Application No. PCT/IB2019/052427, mailed on Sep. 29, 2020, 6 pages.
(Continued)

*Primary Examiner* — Phillip A Gray
(74) *Attorney, Agent, or Firm* — Dorsey & Whitney LLP

(57) ABSTRACT

A space-saving, autonomous power supply enables a monitoring unit to monitor a minimum number of delivery events of a drug delivery device. The monitoring unit has delivery status sensing means for monitoring a device delivery status, a status indicator with an indicator element such as an LED controllable to indicate delivery or module status to a user, and a power supply supplying power to the status sensing means and status indicator of the monitoring unit. The power supply has a peak current source, in particular a rechargeable battery or accumulator, providing a load current for operating the status sensing means and status indicator of the monitoring unit. The power supply has a recharge circuit with a converter and a charging resistor for providing a limited recharge current to the peak current source, plus a recharge source for repeatedly providing an optimized recharge source current to the recharge circuit.

20 Claims, 4 Drawing Sheets

(52) U.S. Cl.
CPC ... *A61M 2205/52* (2013.01); *A61M 2205/581* (2013.01); *A61M 2205/582* (2013.01); *A61M 2205/583* (2013.01); *A61M 2205/587* (2013.01); *A61M 2205/8212* (2013.01)

(58) Field of Classification Search
USPC .......................................................... 604/506
See application file for complete search history.

(56) References Cited

U.S. PATENT DOCUMENTS

| | | | |
|---|---|---|---|
| 6,658,577 | B2 | 12/2003 | Huppi et al. |
| 6,743,202 | B2 | 6/2004 | Hirschman et al. |
| 9,492,620 | B2 | 11/2016 | Schabbach et al. |
| 9,774,749 | B1 | 9/2017 | Skrainar et al. |
| 10,967,133 | B2 * | 4/2021 | Pedersen ........... A61M 5/31583 |
| 2002/0178388 | A1 | 11/2002 | Huppi et al. |
| 2007/0046255 | A1 | 3/2007 | Kim |
| 2008/0278221 | A1 | 11/2008 | Rowland |
| 2010/0069830 | A1 | 3/2010 | Grigorov |
| 2011/0270188 | A1 | 11/2011 | Caffey et al. |
| 2012/0089114 | A1 | 4/2012 | Hemond et al. |
| 2016/0047685 | A1 | 2/2016 | Blei et al. |
| 2017/0368256 | A1 | 12/2017 | Nessel et al. |
| 2018/0043105 | A1 | 2/2018 | Nazzaro et al. |
| 2018/0064881 | A1 | 3/2018 | Whalley et al. |

FOREIGN PATENT DOCUMENTS

| | | |
|---|---|---|
| EP | 3545992 A1 | 10/2019 |
| EP | 3545993 A1 | 10/2019 |
| WO | 2004023637 A1 | 3/2004 |
| WO | 2008049609 A1 | 5/2008 |
| WO | 2011022850 A2 | 3/2011 |
| WO | 2016118736 A1 | 7/2016 |
| WO | 2016142727 A1 | 9/2016 |
| WO | 2017148857 A1 | 9/2017 |
| WO | 2018036938 A1 | 3/2018 |
| WO | 2018041798 A1 | 3/2018 |
| WO | 2018064784 A1 | 4/2018 |
| WO | 2019186381 A1 | 10/2019 |
| WO | 2019186412 A1 | 10/2019 |
| WO | 2019186413 A1 | 10/2019 |

OTHER PUBLICATIONS

International Preliminary Report on Patentability received for International Application No. PCT/IB2019/052470 mailed on Sep. 29, 2020, 9 pages.
International Preliminary Report on Patentability received for International Application No. PCT/IB2019/052471, mailed on Sep. 29, 2020, 9 pages.
International Search Report and Written Opinion received for International Application No. PCT/IB2019/052470 mailed on Jun. 13, 2019, 13 pages.
International Search Report and Written Opinion received for International Application No. PCT/IB2019/052427, mailed on Jun. 17, 2019, 10 pages.
Extended European Search Report issued in European Patent Application No. 18164896.5, mailed on Jul. 2, 2018, 8 pages.
Extended European Search Report received for European Application No. 18164906.2, mailed on Oct. 10, 2018, 6 pages.
English Translation of Chinese publication No. 101120618 A, provided by the European Patent Office with the issuance of the Extended European Search Report.
International Search Report and Written Opinion received for International Application No. PCT/IB2019/052471, mailed on Jun. 13, 2019, 14 pages.
Extended European Search Report received for European Application No. 18164883.3, mailed on Nov. 15, 2018, 8 pages.

* cited by examiner

POWER SUPPLY FOR DRUG DELIVERY SYSTEMS

CROSS-REFERENCE TO RELATED APPLICATIONS

This application is a continuation of International Patent Application No. PCT/M2019/052471, filed Mar. 27, 2019, entitled "POWER SUPPLY FOR DRUG DELIVERY SYSTEMS," which in turn claims priority to European Patent Application No. 18164883.3, filed Mar. 29, 2018, entitled "POWER SUPPLY FOR DRUG DELIVERY SYSTEMS", each of which is incorporated by reference herein, in the entirety and for all purposes.

FIELD OF THE INVENTION

The present invention relates to drug delivery systems for delivering, administering, injecting, infusing or dispensing liquids comprising a drug, medicament, or active ingredient. One variant of the invention begins from an electronic module attachable to a disposable injection device.

BACKGROUND OF THE INVENTION

A variety of diseases exist that require regular treatment by subcutaneous administration of a medicament, and a number of drug delivery devices have been developed to support a patient in accurately and controllably delivering an amount of drug in a self-administration process. Delivery devices include injection devices that are removed from the injection site after each medication event or drug delivery process, as well as infusion devices with a cannula or needle that remains in the skin of the patient for a prolonged period of time. Disposable delivery devices are adapted to deliver a drug from a container such as a pre-filled syringe that is not intended to be replaced or refilled by the patient. Reusable, semi-reusable, or hybrid delivery devices have at least a container and possibly also a container holder that may be replaced by the patient, or a cartridge that may be refilled, while some components of the device may be reused with the replaced or refilled drug container. By way of example, diabetes may be treated by administration of insulin by the patients themselves with the help of multi-variable-dose insulin injection pens or infusion pumps.

Fixed dose disposable injection devices include single-dose injection devices such as auto injectors or patch injectors as well as multi-dose injection devices such as fixed dose injectors. Auto-injectors automatically deliver a fixed dose of liquid drug from a pre-filled syringe by means of a pre-loaded injection spring powering a piston rod and shifting a piston in a syringe barrel. Patch injectors or ready-to-use, pre-filled wearable bolus injectors are applied or adhered to the skin of the patient in view of a single dose injection taking between thirty seconds and several minutes. Fixed-dose injectors have a single, non-variable dosage volume, or may provide a limited number of fixed, non-variable injection dosage volumes for the user to choose from.

Disposable delivery devices may be complemented by a monitoring or control unit being part of a reusable electronic module or auxiliary device adapted to be attached successively to the device housings of plural disposable delivery devices. The monitoring unit serves to monitor the delivery process, in order to proactively prevent or retroactively recognize incorrect handling of the device and to keep track of the doses already applied. In addition to generating data related to an instantaneous status, condition, or use of the delivery device, information on the drug type, cartridge batch, and/or expiration date may be evaluated by the monitoring unit. To that end, the electronic module comprises a delivery status sensing unit for tracking a progress of a medication event performed by means of the delivery device and/or for reading drug information that is stored on a machine-readable tag mounted to the device housing. The module may further comprise a status indicator for signaling status and drug information to a user, and a wireless communication unit for communicating status and drug information to a nearby mobile device or medical gateway. All these units are supplied with power from an energy storing unit of the electronic module, wherein the electronic module generally excludes any kind of electrically powered mechanical actuator or motor load. An exemplary electronic module with a sensing unit capable of discerning various operational states of a disposable auto-injector is disclosed in PCT/CH2017/050004.

A monitoring or control unit with the aforementioned sensor, indicator and communication functionalities may be part of a reusable electronic delivery device and as such be integrated into a device housing of the delivery device comprising the reusable components. In this case, the electronic delivery device may be a reusable injection pen with a monitoring unit and a manually powered delivery drive requiring a user to manually provide the energy to move the piston or to load a drive spring. The electronic delivery device may also be a reusable infusion pump with a monitoring unit and with a motor driving the piston automatically. All sensing, reading, evaluating, indicating, data processing, and communicating facilities of the monitoring module are powered from an energy storing unit of the reusable delivery device.

The abovementioned status indicators, including LEDs or other optical indicators located on a device housing for convenient observation, are frequently used in portable electronic modules or devices of a drug delivery system, and as such have to be active for extended periods of time. Quite often, the status indicators require peak currents that exceed those of the other sensing and processing elements of the monitoring unit, specifically if optical indicators have to be visible in broad daylight. The indicator LEDs may thus account for a considerable share of total energy consumption. Energy management becomes vital if an intended lifetime of an electronic module or of a delivery device equipped with a monitoring unit is to be achieved without undue investments in battery size or quality, specifically when sourcing from autonomous energy storing units that are not intended to be replaced or recharged during lifetime of the monitoring unit.

In the context of drug delivery systems, the load or activity profile of an electronic module or delivery device with a monitoring unit, after initial putting into service, comprises a succession of load cycles corresponding to distinct medication or delivery events and separated by idle or stand-by periods with no delivery activity. Each load cycle has a duration of a few minutes, while the idle periods may last for a few days, with a total number of a few hundred medication events during a service time of a few years. Accordingly, the energy storing unit has to be reliable, provide a storage capacity sufficient for the intended number of load cycles, be capable of delivering peak currents in excess of 100 mA during relatively short periods of time, while limiting space requirements to a minimum. Straightforward conservative dimensioning of the energy storing unit however may be costly, space demanding, increase leakage losses, and/or be impractical for other reasons.

WO/2008/049609 discloses a power supply for a medical appliance such as an insulin pump having a first replaceable energy source for supplying electrical energy to a load such as a pump, a second energy source for bridging supply gaps from the first energy source, and a charging appliance which is fed from the first energy source and ensures that the second energy source has an adequate state of charge. The second energy source comprises a high-capacity double-layer capacitor element that is operated via a voltage converter in parallel with the first energy source, ensuring an uninterruptible power supply for the medical appliance, if the first energy source fails or is being replaced.

WO/2011/022850 discloses an uninterruptible power supply for a medical administration appliance, with a replaceable or rechargeable battery as a first energy source and a rechargeable lithium polymer storage battery as a second energy source. A first current path is used to route energy from the second energy source to a motor load with intermittent current peaks. A second current path with a charging circuit including a resistor is used to permanently route charging energy from the first energy source to the second energy source and to thereby charge the second energy source. A third current path with a highly nonlinear characteristic is used to route load energy from the first source to the motor load such that in an emergency mode caused by a faulty or electrically isolated second energy source, the load may be seamlessly supplied with energy via the third current path. The maximum flow of load energy is not limited via the charging circuit and thus larger than the maximum flow of charging energy. The medical administration appliance typically is a portable or wearable insulin pump with an appliance display and an alarm unit likewise sourced from the uninterruptible power supply.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medically active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

DESCRIPTION OF THE INVENTION

It is an objective of the invention to provide a space-saving, autonomous power supply, enabling a monitoring unit to monitor a minimum number of delivery events of a drug delivery device. This objective is achieved by an electronic module with a power supply and by a method of operating a power supply according to the present disclosure. Various embodiments are evident from the accompanying patent claims.

According to the invention, an electronic module is provided for removable attachment to a device housing of a disposable drug delivery device holding a container with a liquid drug. The electronic module includes a monitoring unit with a delivery status sensing means for monitoring a delivery status of the delivery device, a status indicator with an indicator element such as a Light Emitting Diode (LED) controllable or controlled to indicate a delivery or module status to a user, and a power supply for supplying power to the sensing means and the status indicator of the electronic monitoring unit.

The power supply comprises a peak current source, in particular a rechargeable battery or accumulator, providing or sourcing a load current for operating the sensing means and the status indicator of the electronic monitoring unit. The power supply comprises a recharge circuit with a charging resistor for providing a limited recharge current to the peak current source, as well as a recharge source for repeatedly providing an optimized recharge source current to the recharge circuit.

In a one variant of the electronic module the recharge source is mounted in, or fixed to, the electronic module in a non-replaceable and non-rechargeable manner as a total lifetime energy source. The recharge source is not intended to be non-destructively replaced or recharged by a user, and may be charged ex works to a nominal capacity sufficient for monitoring a pre-defined number of delivery events performed by a plurality of drug delivery devices to which the electronic module is successively attached during an intended module lifetime. As such lifetime charge provision requirement is decoupled from the peak current task of the power supply according to the disclosure, proven button cell technology as the primary recharge source that provides the charge required for the intended number of operations at low cell volume and acceptable pricing may be employed. The high internal resistance of these button cells is circumvented and/or compensated by the peak current source with low internal resistance and by the recharge circuit with voltage conversion to feed the peak power source. The recharge current provided by the recharge circuit is limited by the charging resistor and always gives rise to an operational recharge source current not exceeding, on average, a nominal recharge source current compatible with a capacity-preserving requirement of the recharge source.

In one variant of the electronic module the recharge source is exclusively connected to the peak current source and to the load via the entire recharge circuit, including the current limiting charging resistor. The power supply is devoid of any backup connection between the recharge source and the load that would bypass or otherwise omit the charging resistor of the recharge circuit, and that would require additional passive or even active elements for controlling current flowing in the backup connection. In accordance with the fact that the peak current source is not replaceable, reliability thereof has to be proven intrinsically, such that there is no need to anticipate a potential failure thereof by additional complexity of the supply circuitry. In other words, the recharge source is not diverted to power the status indicator and/or to supplant the peak current source.

In another variant an upper limit of a nominal recharge source current is defined as being capable of draining or extracting at least 70%, alternatively at least 80%, or alternatively at least 90% of a nominal charge capacity of the recharge source. The peak current source is adapted to provide a peak current to the load that exceeds the nominal recharge source current temporarily by a factor of at least 20, alternatively by a factor of at least 50, or alternatively by a factor of at least 100.

In one embodiment, the recharge circuit may include an electronic converter for converting a recharge source voltage to a recharging voltage of the charging resistor. A recharge controller for controlling the recharge circuit, specifically the electronic converter, is configured to recharge the peak current source exclusively upon completion of a delivery or medication event performed by means of the delivery device to which the electronic module is attached, and monitored by means of the monitoring unit. In this context, the recharge controller may be connected to a status sensor of the monitoring unit or otherwise may receive status information from a status sensor indicative of an end of delivery.

In a further embodiment, a nominal cycle charge of a single load cycle is defined as the charge demanded by the monitoring unit during a regular load cycle to perform according to plan, and preferably excludes a charge or energy that may be supplied to any extras such as alarm elements that are not intended to be active in normal operation. The peak current source may be dimensioned with a capacity that exceeds the nominal cycle charge by a factor of at least 10, alternatively at least 20. The sensing means and the status indicator of the monitoring unit are specified to operate at or above a minimum load voltage $U_{L,min}$. The recharge controller is configured to recharge the peak current source to an extent that allows providing, by the peak current source during the subsequent delivery event or load cycle, the nominal cycle charge while maintaining a load voltage $U_L$ above the minimum load voltage $U_{L\_min}$. In other words, the minimum load voltage $U_{L,min}$ determines an operating or working point of the peak current source, and a cyclic or repeating recharging activity is limited to a provision of the nominal cycle charge rather than determined by a fixed recharge time.

Accordingly, a zero-load peak current source voltage $U_{PCS}$ during and in particular at the end of the charging activity is likewise kept at a minimum value, which allows the recharging voltage $U_{C,out}$ to be small yet above the zero-load peak current source voltage $U_{PCS}$. A low value of the recharging voltage $U_{C,out}$ reduces the recharge source current and benefits the capacity preservation of the recharge source. On the other hand, a small recharge current may lead to a lower efficiency of the electronic converter. Therefore the resistance of the charging resistor is ultimately chosen to balance converter efficiency, recharge time, and recharge source capacity preservation requirements. Ultimately, the proposed recharging strategy with a minimized zero-load peak current source voltage $U_{PCS}$ increases a lifetime of the peak current source, reduces leakage currents, and eliminates a need for a peak current source overload control that would be indispensable if the peak current source were charged to a maximum. In consequence, the power supply is adapted to terminate the recharge activity well within a nominal idle period between two successive delivery events, and the recharge circuit is controlled to not supply a recharge current during a load cycle.

In another embodiment, the recharge controller is configured to control the recharge circuit to generate a converter output voltage $U_{C,out}$ that is constant during the recharge activity. The converter output voltage $U_{C,out}$ is sufficiently higher than a maximum zero-load peak current source voltage $U_{PCS}$ to cause a decent residual voltage drop and recharge current across the charging resistor towards the end of the recharge activity. Alternatively, a variable converter output voltage maintaining for instance a constant voltage drop across the charging resistor may be possible.

In other embodiments, the peak current source and the recharge source are of predominantly flat shape, defining each a main plane, and arranged or stacked adjacent to each other with the two main planes in parallel. The peak current source and the recharge source may in this case be electrically connected to and supported by a same Printed Circuit Board (PCB). Preferably, the electronic module has a module housing with a part or volume accommodating the monitoring unit and adapted to be placed adjacent to a proximal or rear end surface of an elongate auto-injector, with the stacked peak current source and recharge source arranged perpendicular to a main axis of the elongate auto-injector. This results in a space-saving arrangement with a minimum extra extension of the auto-injector/module in the direction of the main axis.

According to an embodiment, a method of operating a power supply for a monitoring unit of a reusable electronic module or of a drug delivery' device is proposed. The monitoring unit comprises delivery status sensing means for monitoring a delivery status, a status indicator for indicating the delivery status, and the power supply for supplying power to the sensing means and the status indicator, the power supply comprising a peak current source for providing a load current to the sensing means and the status indicator, a recharge circuit with a charging resistor for providing a recharge current to the peak current source, and a recharge source for providing a recharge source current to the recharge circuit. The method comprises, by a recharge controller for controlling the recharge circuit, initiating a recharge activity on behalf of the peak current source upon completion of a delivery event, generating a constant converter output voltage, and/or recharging the peak current source to an extent sufficient for provision, during the subsequent delivery event, of a nominal cycle charge without a peak current source voltage dropping below a minimum load voltage. In this context, the nominal cycle charge corresponds to the charge or energy consumed by the monitoring unit during a regular delivery event.

According to the disclosure, a power supply for supplying power to elements of an electronic monitoring unit of a mobile and reusable drug delivery device provided with a replaceable container for a liquid drug is proposed. The monitoring unit includes delivery-status sensing means for monitoring a delivery status of the delivery device, and a status indicator for indicating the delivery status. In one embodiment, the power supply is exclusively intended for the monitoring unit, and the supplied load excludes, or is devoid of, any kind of electrically powered mechanical actuator or motor load of the delivery device. The power supply comprises a peak current source for providing a load current to the sensing means and the status indicator, a recharge circuit with a charging resistor for providing a recharge current to the peak current source, and a recharge source for providing a recharge source current to the recharge circuit. In one embodiment of the power supply and monitoring unit, the recharge source is exclusively connected to the monitoring unit via the charging resistor, the recharge source is mounted in the delivery' device in a non-replaceable and non-rechargeable manner, and/or the peak current source is adapted to provide a peak current to the load exceeding temporarily a nominal recharge source current by at least a factor of 20, the nominal recharge source current draining or extracting at least 70% of a nominal charge capacity of the recharge source.

BRIEF DESCRIPTION OF THE DRAWINGS

The subject matter of the invention will be explained in more detail in the following text with reference to preferred exemplary embodiments which are illustrated in the attached drawings, in which.

The reference symbols used in the drawings, and their primary meanings, are listed in summary form in the list of designations below. In principle, identical parts are provided with the same reference symbols in the figures.

DETAILED DESCRIPTION OF PREFERRED EMBODIMENTS

Figure 1:
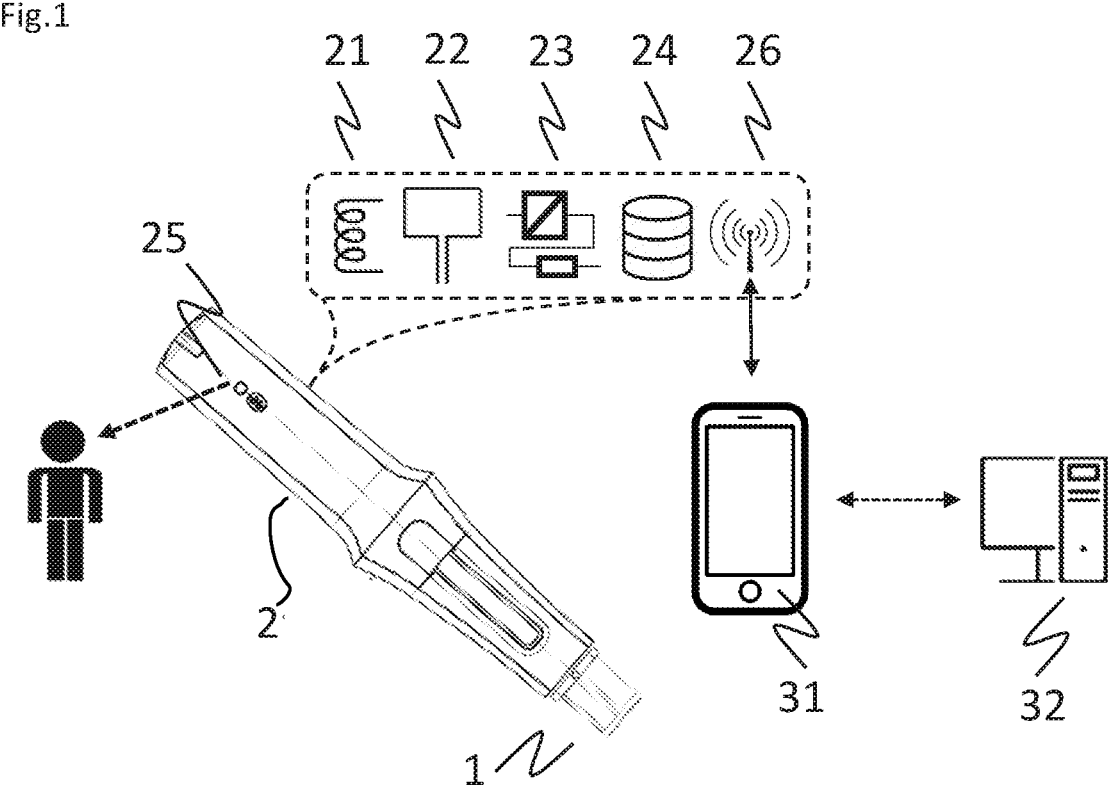
FIG. 1 depicts a variant of a medical monitoring system with an auto-injector.

FIG. 1 depicts an embodiment of a medical monitoring system, comprising an auto-injector as an exemplary disposable injection device 1, an electronic module 2 releasably attached to a device housing of the injection device, and a mobile device 31 such as a smartphone or tablet device running a dedicated application program; or a laptop computer configured accordingly. The mobile device is communicatively connected via a data communication network, e.g. the Internet, to a remote server, cloud based computing facility, or expert system 32. The electronic module 2 comprises a status sensor or a status sensing means including an electrical or mechanical feedback sensor 21 and a tag reader 22 for reading drug information from a tag or label mounted to the device housing. The electronic module further comprises a power supply 23 for supplying power to a status indicator 25. The latter may include an LED, buzzer, vibration alarm, or any other type of HMI element for providing visual, acoustic, or tactile feedback about an injection status such as a progress of an ongoing injection process. A memory or data storage unit 24 is adapted to store status or delivery information. The electronic module also comprises a communication unit 26 for wireless transmission of an injection status or drug status to the mobile device via Bluetooth Low Energy (BTLE) or equivalent short or near range wireless communication technology. The electronic module 2 has a rear, or proximal, part where some or all electronic components as described are located.

Included in a module housing of the electronic module is a lock/release mechanism to secure the attachment of the electronic module to the injection device in order to protect against unintended detachment, specifically during removal of a needle protective cap from the auto-injector. The auto-injector is intended for automatically delivering a fixed dose of liquid drug from a pre-filled syringe by means of a pre-loaded injection spring provided for powering a piston rod and shifting a piston comprised in the syringe. The auto-injector comprises a needle protective sleeve, or cover sleeve, for protecting a needle of the syringe after removal from the injection site. Upon removal of the auto-injector from the injection site the needle protective sleeve is biased to a needle protecting position by a cover sleeve spring, and locked in this position by a locking means generating a locking sound. Start and end of a substance delivery as well as injection device lift-off may be detected by the injection status sensing means and advantageously combined to obtain a characterization of the ongoing injection process or medication event, in order to track whether an injection event has occurred according to the medication schedule but also whether that injection was successfully completed or not. The injection status sensing means may include an electrical sensor such as a contact-free inductive or capacitive sensor. An exemplary inductive sensor may detect initial, intermediate, and final values of, and/or corresponding changes or differences in, a static or alternating magnetic field or flux depending on a position or displacement of a magnetic device component.

The wireless communication unit 26 is connected to the memory or data storage unit 24 and/or to a processing unit, and adapted to wirelessly communicate, specifically upload, injection information to a nearby mobile device or dedicated medical gateway. The injection information may include a time stamp indicative of a time of a medication event as well as the expelled dose or other drug information read from a tag or label mounted to the device housing. The injection information may be transmitted instantaneously, or stored in the memory unit connected to the processing unit, for later upload or batch transfer. The injection information may, in addition or alternatively, include a quality measure of an injection process, such as a binary flag indicating that a minimum holding time requirement has been complied with.

Figure 2:
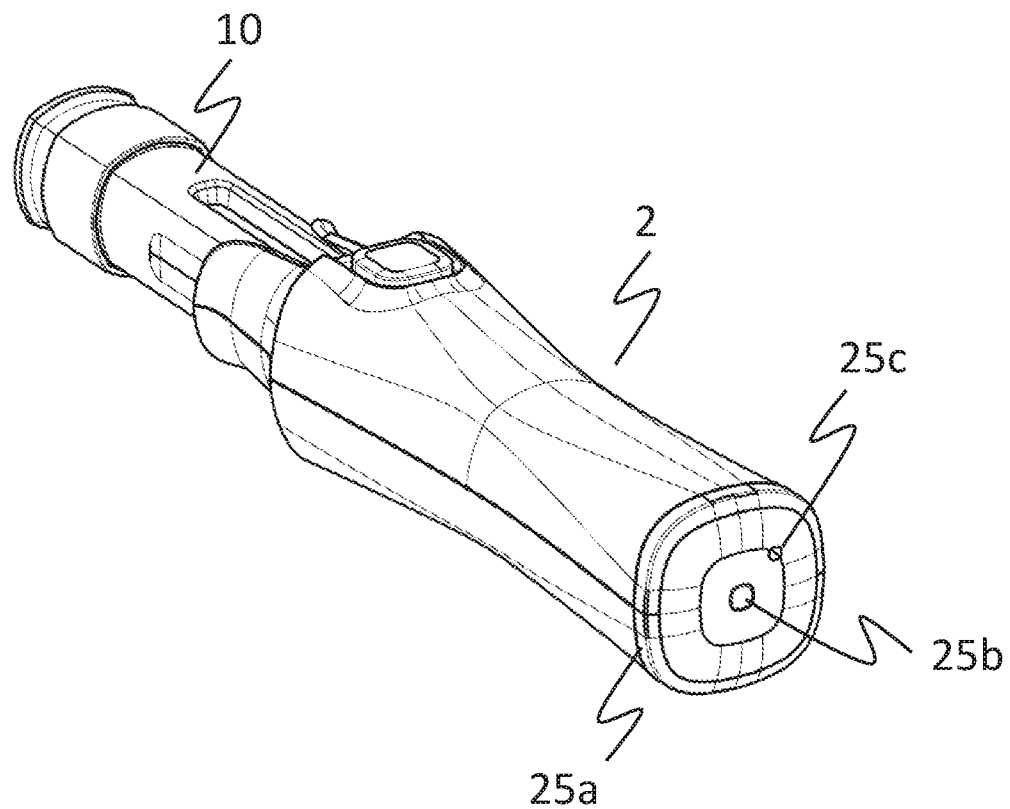
FIG. 2 depicts an electronic module attached to an auto-injector.

FIG. 2 discloses a rear view of a slightly different embodiment of an electronic module 2 mounted to the housing 10 of an injection device. The module includes a spot-shaped status indicator element 25b being located on a rear or proximal end surface of the module, and a ring-shaped status indicator element 25a being located around the proximal edge of the electronic module. Due to its peripheral location, the ring-shaped status indicator 25a is visible even when the module 2 is held by a user, and due to its circumferential shape, may be observed from all sides and under different angles, in particular during delivery when the injection device has been placed adjacent to an injection site. A Bluetooth Low Energy connect status indicator element 25c is further provided to signal a connect status of the communication unit 26.

Figure 3A:
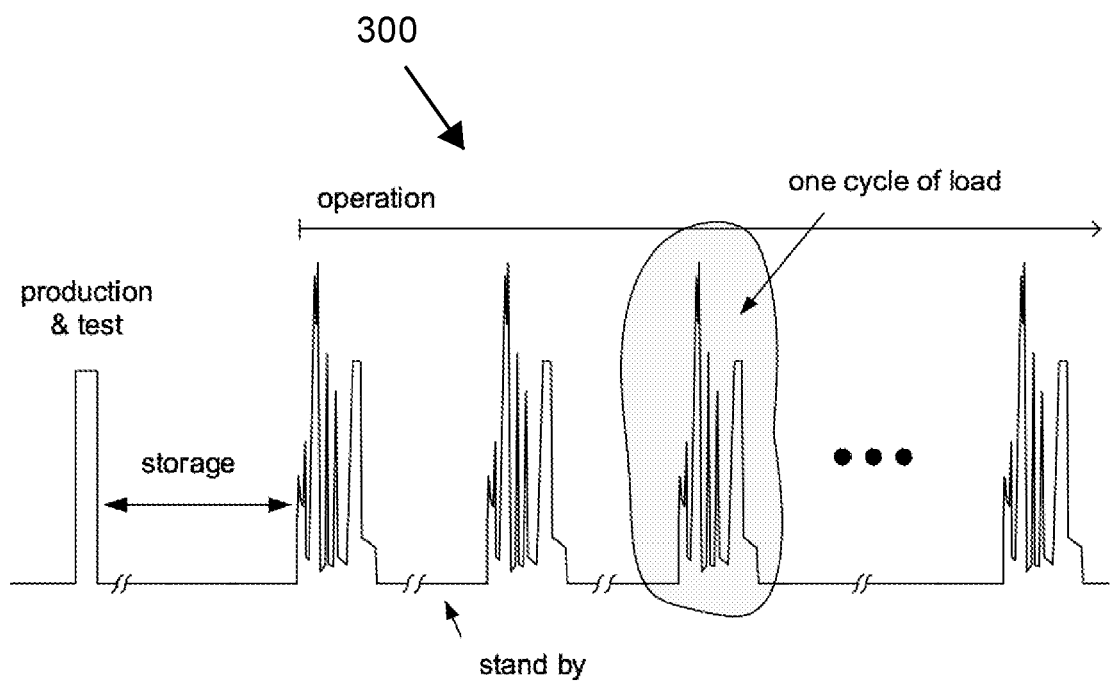
FIGS. 3A and 3B depict load profiles of a monitoring unit.
Figure 3B:
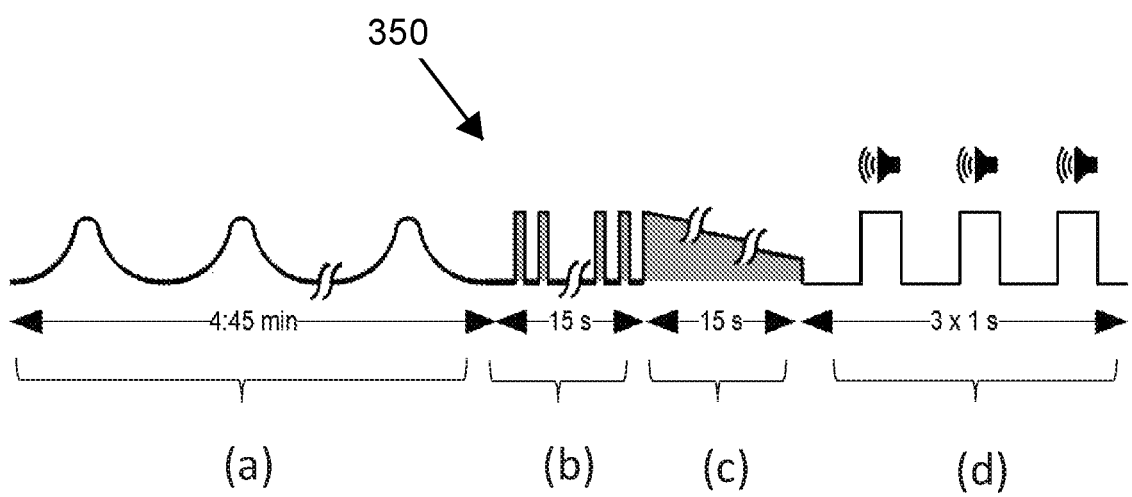

FIG. 3A depicts a schematic load or power demand profile 300 of an electronic module or delivery device with a monitoring unit, starting with a production, assembly and/or testing phase followed by a storage period of up to one year or above. After initial putting into service, a succession of load cycles corresponding to medication or delivery events is indicated, with each load cycle being of a duration of between one and thirty minutes, and with successive load cycles being separated by idle or stand-by periods of a duration of between one hour and one month, preferably between one day and one week. In the present context, one to two load cycles per week for a total service time of two years may be a realistic scenario when sourcing from energy storing units that are not intended to be replaced or recharged during lifetime of the monitoring unit. Apart from and/or following completion of the recharging activity as described, the monitoring unit may be turned off or at least put to sleep during the idle periods, and restarted or woken up at the beginning of a load cycle. FIG. 3B depicts a sample current load profile 350 showing details of a single medication or delivery event, including interval (a) smart LED operation during an initial drug temperature equalization phase with brightness peaks that mimic natural breathing, interval (b) a blinking LED mode during injection of the drug, interval (c) a permanently illuminated LED indicator with a gradually decreasing brightness during a holding period, and interval (d) a buzzer producing three beeps upon completion of the event.

Figure 4:
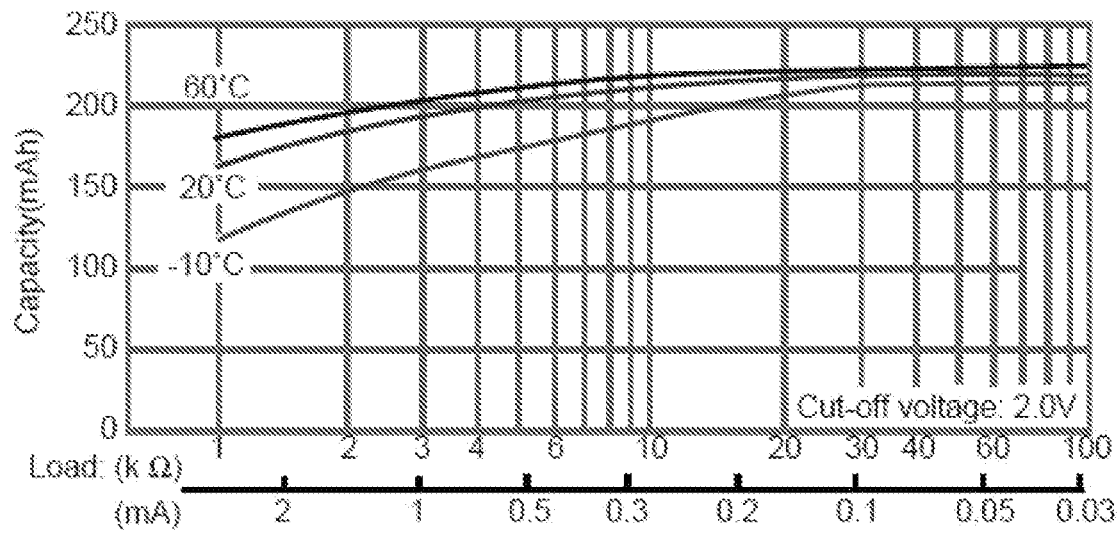
FIG. 4 shows a sample discharging characteristic of a button cell.

FIG. 4 depicts the sample discharging characteristic of a button or coin cell of the CR2032 type. A nominal capacity of 230 mAh is only obtained for small cell-discharge currents, and at least 80% of the nominal capacity may be sourced from the button cell as long as a nominal cell-discharge current remains below 1 mA, preferably below 0.3 mA. Similar nominal cell-discharge currents permitting a reasonable percentage of the nominal charge to be extracted may be defined for any type of battery to serve as nominal recharge source currents in the context of the present invention.

Figure 5:
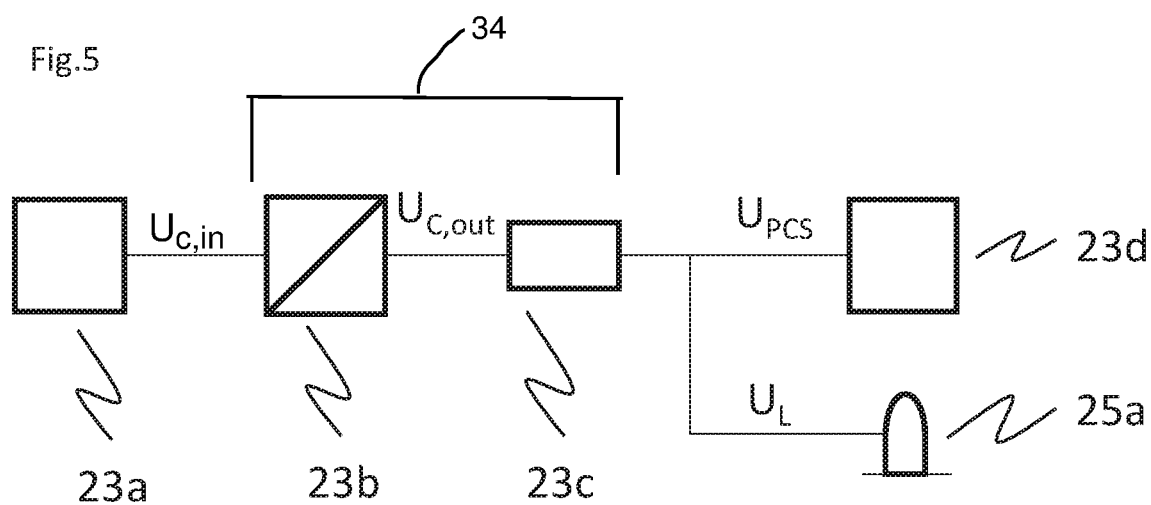
FIG. 5 depicts a power supply circuit according to an embodiment of the invention.

FIG. 5 depicts a power supply circuit according to an embodiment of the invention. A recharge source 23a with a nominal charge source capacity and a nominal voltage is connected, and providing a recharge source current, to a recharge circuit 34. The recharge circuit 34 includes a charging resistor 23c and a DC/DC electronic converter 23b for converting an operational recharge source voltage $U_{C,in}$ to a recharging voltage $U_{C,out}$ at an output port of the DC/DC converter 23b. The charging resistor 23c is connected to the converter 23b output port and to a peak current source 23d, and conveys, during recharge activity, a recharge current to the peak current source 23d at a zero-load peak current source voltage $U_{PCS}$. The peak current source 23d is finally connected to a load 25a of a monitoring unit for providing or sourcing, during a load cycle, a load current at a load voltage $U_L$ to the elements of the electronic monitoring unit.

The DC/DC electronic converter 23b may include a high frequency transformer, or be omitted altogether in case the recharging voltage at the charging resistor 23c is equal to the nominal voltage of the recharge source 23a. The peak current source 23d may be connected to a low-dropout or LDO regulator, that is, a DC linear voltage regulator adapted to regulate an LDO output load voltage that is close to a LDO supply or peak current source voltage. Alternatively the LDO can be replaced by a simple switch element, e.g. a transistor. Auxiliary circuits for protecting the peak current source 23d against short circuits and for minimizing a leakage current of the recharge source prior to a first load cycle and during idle periods may likewise be added.

Preferably, the load supplied by the power supply is limited to the monitoring unit and specifically excludes a motor load or other electrically powered mechanical actuator with moving parts, a possible automated drug delivery of a delivery device in this case being powered by a source of energy distinct from the power supply. In some embodiments, and in accordance with the fact that the maximum recharge current provided by the recharge circuit is not capable of sourcing the load, the connection between the peak current source 23d and the load is permanent throughout the entire lifetime of the power supply, in particular devoid of a load shed switch or the like that would allow to isolate the peak current source from the load. In some embodiments, the power supply is devoid of any sensor for monitoring a state of charge of the recharge source, as the recharge source is not intended to be replaced in the first place, and because the timing of the recharge activity is not dependent on such state of charge.

The recharge source 23a may be a regular Li-based button cell, e.g. of the CR 2032 type with a nominal recharge source capacity of 230 mAh and a nominal cell voltage $U_{C,in}$ of 3 V. The peak current source 23d may be a rechargeable battery or accumulator, preferably of a LiFePO4 type, or a Lithium Polymer (LiPo) battery with a rated output voltage of approximately 3.3-3.6 V if phosphate-based, or 3.6-4.0 V if Ni, Co, Mg based, with a typical nominal capacity of about 30 mAh. The DC/DC converter 23b is an electronic converter realized as an integrated circuit on a chip, with a converter controller arranged and configured to control operation of the DC/DC converter to convert the nominal cell voltage to a recharging voltage $U_{C,out}$ of an exemplary value of 3.75 V. The voltage drop between the recharging voltage $U_{C,out}$ and the peak current source voltage $U_{PCS}$ during recharge is caused by the charging resistor of a resistance between 10 and 1000 Ohm, suitably chosen to limit the recharge current, and ultimately to limit the recharge source current to a value below the nominal recharge current. During a single load cycle, a nominal cycle charge of approximately 1 mAh may be provided by the power supply.

Figure 6:
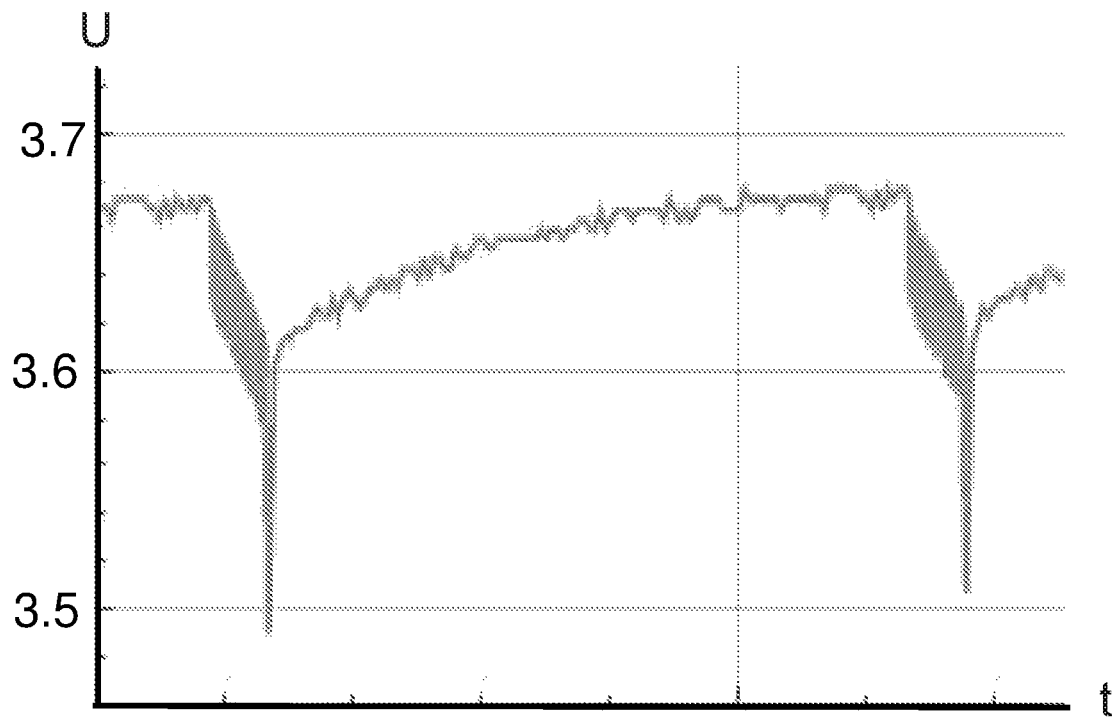
FIG. 6 shows a measured voltage at a peak current source versus time.

FIG. 6 depicts a measured voltage at a peak current source versus time of a trial operation covering two successive delivery events spaced by an idle period of approximately one hour. The corresponding load cycles start off at a load voltage $U_L$ of approximately 3.68 V with a number of LED operations and terminate with three buzzer signals that cause the load voltage $U_L$ to drop to a value of approximately 3.5 V. Instantaneously after the last buzzer signal, the peak current source voltage recovers to a zero-load value $U_{PCS}$ of approximately 3.6 V, when the recharging activity sets in and gradually lifts the zero-load voltage to the maximum zero-load value.

Figure 7:
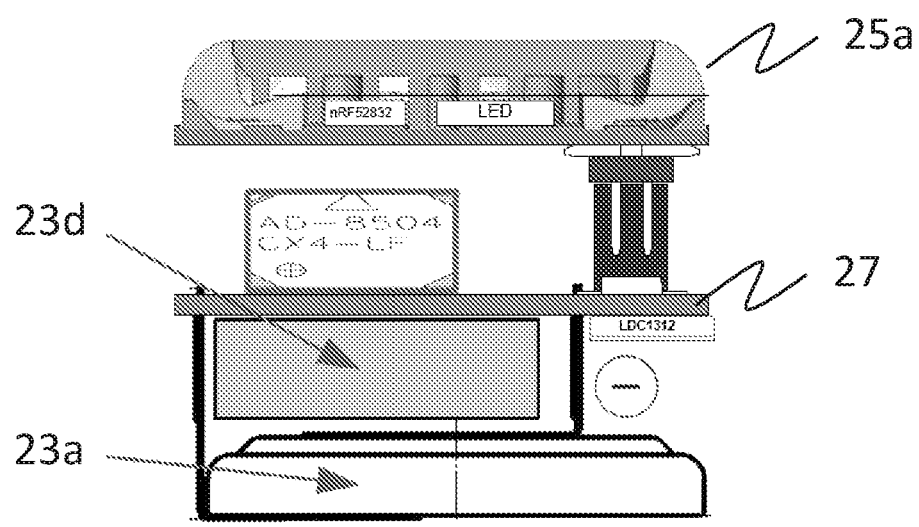
FIG. 7 is a side view of a geometrical arrangement of the elements of a power supply.

FIG. 7 depicts a side view of a geometrical arrangement of the elements of the power supply. The recharge source 23a is a disc-shaped circular button cell of the CR 2032 type, and the peak current source 23d is a flat, rectangular, cushion-shaped LiPo battery. The button cell and the LiPo are arranged adjacent to each other in a co-planar manner, forming a source stack with minimum extension. The stack as well as the recharge circuit are mounted on a Printed Circuit Board PCB 27. In case of an electronic module attached to a delivery device such as an auto-injector, the PCB and the co-planar source stack may be arranged in a rear, or proximal, part of the module, and oriented perpendicular to a main, longitudinal axis of a delivery device that corresponds the vertical axis in FIG. 7.

The status indicator of the electronic module or of the delivery device comprises a visual, audible and/or tactile status indicator element as a human interfacing means. The indicator element may include a single multicolor LED or a loudspeaker for generating language-independent sounds or simple melodies. The status indicator may explicitly exclude any advanced human-machine interfacing capability. In particular, the status indicator may be devoid of a display, screen, or projector for visually transmitting readable instructions, and likewise exclude an artificial speech assistant for reading out loud the instructions. Such advanced HMI functionality including elaborate graphic display and speech output capabilities may be provided by a mobile device communicatively connected to the electronic module or delivery device. To that end, the electronic module or the delivery device may comprise a communication unit R? to transmit the status information to a mobile device such as a smartphone or tablet device running a dedicated application program, or a laptop computer configured accordingly.

Communication to the mobile device may preferably take place via Bluetooth Low Energy (BTLE) or equivalent short or near range wireless communication technology.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

1 Delivery device
10 Device housing
2 Electronic module
21 Inductive sensors
22 Tag reader
23 Power supply
23a Recharge source
23b Converter
23c Charging resistor
23d Peak current source
24 Memory unit
25 Status indicators
26 Communication unit
27 Printed Circuit Board
31 Mobile device
32 Remote server
34 Recharge circuit

The invention claimed is:

1. An electronic module for removable attachment to a device housing of a disposable delivery device configured for holding a container with a liquid drug, said module comprising:
 delivery status sensing means for monitoring a delivery status;
 a status indicator for indicating the delivery status, wherein the status indicator is free of a graphical display; and
 a power supply being configured for supplying power to the sensing means and the status indicator, wherein the power supply comprises:
  a peak current source configured as a rectangular LiPo battery for providing a load current to a load comprising the sensing means and to the status indicator;
  a recharge circuit with a charging resistor for providing a recharge current to the peak current source; and
  a recharge source configured as a button cell battery for providing a recharge source current to the recharge circuit,
  wherein the load current is higher than the recharge source current.

2. The electronic module of claim 1, wherein the recharge source is mounted in a non-replaceable and non-rechargeable manner.

3. The electronic module of claim 1, wherein the recharge source is exclusively connected to supply the load current via the charging resistor.

4. The electronic module of claim 1, wherein at least 70% of a nominal charge capacity of the recharge source is drainable by a nominal recharge source current, and the power supply is adapted to supply a peak load current exceeding the nominal recharge source current by at least a factor of 20.

5. The electronic module of claim 1, further comprising a recharge controller for controlling the recharge circuit, wherein the recharge controller is configured to start recharging the peak current source upon completion of a delivery event.

6. The electronic module of claim 5, wherein the peak current source provides a nominal cycle charge during a regular delivery event, wherein the recharge controller is configured to recharge the peak current source for provision, during a next delivery event, of the nominal cycle charge at a peak current source voltage above a minimum load voltage.

7. The electronic module of claim 5, wherein the recharge circuit comprises a converter with a converter output port connected to the charging resistor, wherein the recharge controller is configured to control the converter to generate a constant converter output voltage.

8. The electronic module of claim 1, wherein the peak current source and the recharge source are of predominantly flat shape, and wherein the peak current source and the recharge source are arranged adjacent to each other in two parallel planes.

9. The electronic module of claim 8, wherein the electronic module comprises a module housing with a part adapted to be placed next to a proximal end of an elongate delivery device, characterized in that the two parallel planes are arranged perpendicular to a main axis of the elongate delivery device.

10. A method of operating a power supply of a delivery device monitoring unit comprising delivery status sensing means for monitoring a delivery status, a status indicator for indicating the delivery status, the status indicator being free of a graphical display, and the power supply for supplying power to the status sensing means and the status indicator, the power supply comprising a peak current source configured as a rectangular LiPo battery for providing a load current to the status sensing means and the status indicator, a recharge circuit with a charging resistor for providing a recharge current to the peak current source, and a recharge source configured as a button cell battery for providing a recharge source current to the recharge circuit, the method comprising:
 recharging the peak current source only upon completion of a delivery event,
 wherein the load current is higher than the recharge source current.

11. The method of claim 10, wherein the peak current source provides a nominal cycle charge during the delivery event, the method further comprising:
 recharging the peak current source for provision, during a next delivery event, of the nominal cycle charge at a peak current source voltage above a minimum load voltage.

12. The method of claim 10, further comprising controlling the recharge circuit to generate a constant converter output voltage.

13. A power supply for an electronic monitoring unit including delivery status sensing means for monitoring a delivery status, a status indicator for indicating the delivery status, the status indicator being free of a graphical display, the power supply supplying power to the status sensing means and the status indicator and comprising:
- a peak current source for providing a load current to the status sensing means and the status indicator,
- a recharge circuit with a charging resistor for providing a recharge current to the peak current source, and
- a recharge source configured as a button cell battery for providing a recharge source current to the recharge circuit, wherein the recharge source is connected to the status indicator exclusively via the charging resistor, wherein the load current is higher than the recharge source current.

14. The power supply of claim 13, wherein the recharge source is mounted in a non-replaceable and a non-rechargeable manner.

15. The power supply of one of claim 13, wherein at least 70% of a nominal charge capacity of the recharge source may be drained by a nominal recharge source current, and wherein the power supply is adapted to supply a peak load current exceeding the nominal recharge source current by at least a factor of 20.

16. The power supply of claim 13, further comprising a recharge controller for controlling the recharge circuit, wherein the recharge controller is configured to start recharging the peak current source upon completion of a delivery event.

17. The power supply of claim 13, wherein the peak current source provides a nominal cycle charge during a regular delivery event, wherein the recharge controller is configured to recharge the peak current source for provision, during a next delivery event, of the nominal cycle charge at a peak current source voltage above a minimum load voltage.

18. The power supply of claim 13, wherein the recharge circuit comprises a converter with a converter output port connected to the charging resistor, wherein the recharge controller is configured to control the converter to generate a constant converter output voltage.

19. The power supply of claim 13, wherein the peak current source and the recharge source are of predominantly flat shape, wherein the peak current source and the recharge source are arranged adjacent to each other in two parallel planes.

20. The power supply of claim 19, wherein the monitoring unit comprises a housing with a part adapted to be placed next to a proximal end of an elongate delivery device, wherein the two parallel planes are arranged perpendicular to a main axis of the elongate delivery device.

* * * * *